United States Patent [19]
Altman

[11] Patent Number: 6,012,171
[45] Date of Patent: Jan. 11, 2000

[54] APPARATUS FOR PROTECTION DURING THE USE OF HAIR DYE OR COLORING

[76] Inventor: Jason S. Altman, 8799 Escondido Way E., Boca Raton, Fla. 33433

[21] Appl. No.: 08/995,929

[22] Filed: Dec. 22, 1997

[51] Int. Cl.⁷ ........................................................ A61F 9/00
[52] U.S. Cl. ............................ 2/174; 2/206; 2/9; 132/212
[58] Field of Search .................................. 2/9, 206, 207, 2/174, DIG. 11, 181; 132/212, 213, 214; 128/857

[56] References Cited

U.S. PATENT DOCUMENTS

| | | | |
|---|---|---|---|
| 1,750,937 | 3/1930 | Morgan . | |
| 2,159,435 | 5/1939 | Gribbin | 132/1 |
| 2,226,956 | 12/1940 | Womack | 2/174 |
| 2,987,730 | 6/1961 | Walker | 2/174 |
| 3,388,708 | 6/1968 | Hudson | 132/9 |
| 3,419,909 | 1/1969 | Spain | 2/174 |
| 3,529,308 | 9/1970 | McBride | 2/174 |
| 4,133,052 | 1/1979 | Hodgman et al. | 2/174 |
| 4,368,545 | 1/1983 | Seidman | 2/174 |
| 5,423,091 | 6/1995 | Lange | 2/181 |
| 5,682,607 | 11/1997 | Klein | 2/9 |
| 5,711,026 | 1/1998 | Kaltman et al. | 2/9 |
| 5,867,834 | 2/1999 | Simpson | 2/174 |

FOREIGN PATENT DOCUMENTS

| 1017305 | 1/1966 | United Kingdom | 2/174 |
|---|---|---|---|

*Primary Examiner*—Michael A. Neas
*Attorney, Agent, or Firm*—Oltman, Flynn & Kubler

[57] ABSTRACT

An apparatus for protection of the scalp, facial skin, eyes, mouth and nostrils from hair dye, coloring and other chemical products for hair treatment. The covering includes an absorbent pad designed to be worn against the wearer's forehead so that any liquid runoff from hair treatment is absorbed by the pad. The apparatus preferably includes a substance or device to hold the pad in place, such as an adhesive which attaches the pad to the forehead, or ear handles wherein the pad may be worn as one might wear a pair of goggles. Additionally the pad may be enclosed in an impermeable lining such that any liquid absorbed by the pad may not later escape. Several of these pads may be constructed together to form a continuous series or strip of pads. Each pad is then designed to be easily detachable from the remainder of the series. This facilitates convenient storage and removal of the pads.

10 Claims, 3 Drawing Sheets

APPARATUS FOR PROTECTION DURING THE USE OF HAIR DYE OR COLORING

This invention relates generally to a protective covering, and in particular to a covering device that protects the scalp, facial skin, eyes, mouth and nostrils during the application of dye, coloring or other chemical products for hair treatment.

BACKGROUND OF THE INVENTION

The use of dye, coloring or other chemical products to enhance hair appearance can have adverse results such as skin staining, particularly in the forehead region. Due to the unappealing effects of such staining, it is important that adequate measures be taken to protect against these occurrences. Previously, hairdressers have applied protective creams to the forehead skin, just below the hairline. This method of stain prevention is often ineffective and does not protect the facial skin, eyes, mouth and nostrils from the chemical products used in hair dying, coloring or other treatment. These creams can cause rashes, blemishes, scarring, or other irritations and allergic reactions. Additionally, the creams can lead to uneven dying or coloring of the hair roots. The presence of unstained hair roots defeats the purpose of dying or coloring and is an undesirable result.

Presently, there are no consumer products available to effectively prevent facial and forehead skin staining, or run-offs of the hair treatment chemicals to the facial skin, eyes, mouth and nostrils.

Thus, a need exists for protecting the facial skin, as well as the eyes, nose and mouth from hair treatment chemicals, while at the same time allowing the even application of these products to the hair.

SUMMARY OF THE INVENTION

One object of the present invention is to provide an apparatus for protecting the scalp, facial skin, eyes, mouth, and nostrils during the application of dye, coloring or other chemical products for hair treatment.

Another object of the present invention is to provide the aforementioned protections while allowing even application of dying, coloring, or other hair treatment products to the hair.

One embodiment of the protective apparatus includes an absorbent pad with a top edge profiled to follow the average hairline. The pad extends down to cover the wearer's forehead and outwardly toward the wearer's ears. The pad is constructed to act as a highly absorbent chemical retainer. The pad may include some means by which to attach the pad to the user's forehead.

In another embodiment of the invention, the pad is enclosed in a plastic lining. The absorbing material of the pad is left exposed at the top edge of the pad, so that any liquid escaping from the hairline will encounter the absorbent pad and be pulled by the pad's capillary action into the pad and inside the plastic liner. One outer side of the plastic liner has an adhesive material attached such as adhesive tape or other layered adhesive material so that the pad may be fixedly attached to the wearer's forehead.

Another embodiment of the invention includes an absorbent pad designed to conform to the wearer's forehead. This pad is attached to a structure resembling goggles, composed of paper or plastic. The goggles have a flat planar surface designed to hold the pad against the wearer's forehead. At the bottom of this surface are two openings intended for the wearer's eyes. These openings can also be provided with clear plastic lenses to protect the wearer's eyes from chemical exposure. Ear handles are attached to the sides of the flat planar surface and extend outwardly to both sides. These handles are curved such that when folded back at their attachment point, they fit over the wearer's ears, holding the goggles in place. The pad used in these goggles could be designed as any of the aforementioned varieties, with or without a plastic lining.

The preceding pad or goggles could be constructed so that they are attached in series to form a continuous strip. Each apparatus is detachable from the others, enabling the user to take only those needed. This embodiment allows for easy storage and removal of pads or goggles as needed.

DESCRIPTION OF THE PREFERRED EMBODIMENTS

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

Figure 1:
FIG. 1 shows a side view of the invention in position when used.

FIG. 1 shows a side view of the protective apparatus 101 when used. The invention is an absorbent pad to be worn just below the user's hairline. The pad extends down to cover the wearer's forehead and outwardly toward the wearer's ears. The pad is generally a flexible, flat, planar surface, constructed from woolite, cotton, or a polymer material designed to act as a highly absorbent chemical retainer. The pad may be constructed with many fine air gaps which serve as minute capillaries for absorbing liquids, dyes and chemical agents used by hairdressers.

Figure 2:
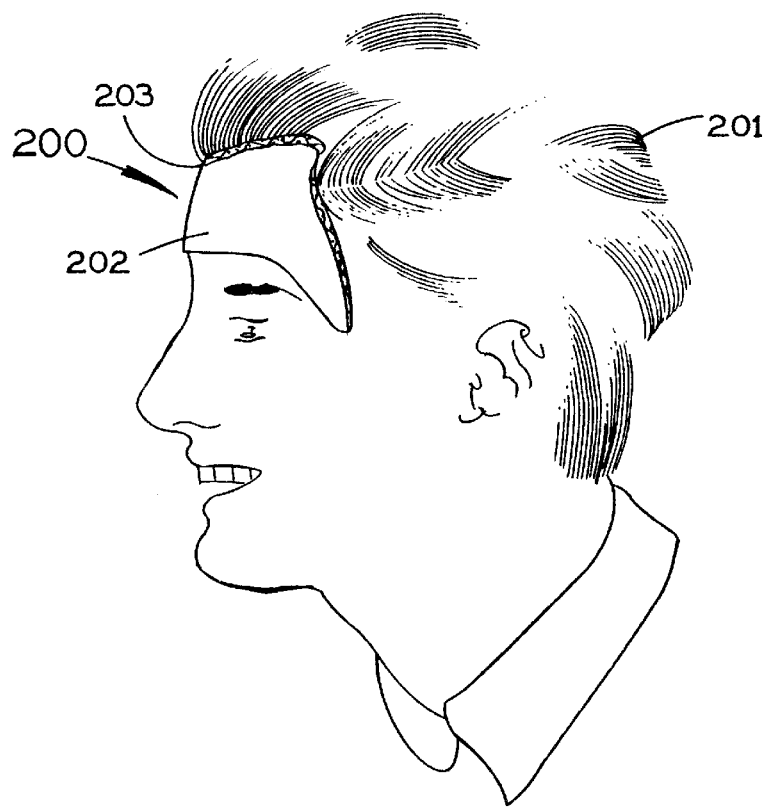
FIG. 2 shows another embodiment of the invention in position when used.

FIG. 2 shows another embodiment of the absorbent pad 200 in position when used. In this embodiment an impermeable lining 202 made of a material such as plastic partially surrounds the absorbent pad on both sides, leaving the top edge of the pad 203 exposed. The impermeable lining functions to contain any liquid absorbed by the pad. Referring to FIGS. 1 and 2, a user 100 or 201 laces the top edge of the pad 203 just beneath the hairline, with the remainder of the pad 200 against the wearer's forehead. The absorbent material of the pad is exposed along its top edge, which is adjacent to the hair line when worn. Any liquid runoff from the chemical hair treatment encounters the exposed absorbent pad and is drawn into the pad.

Figure 3:
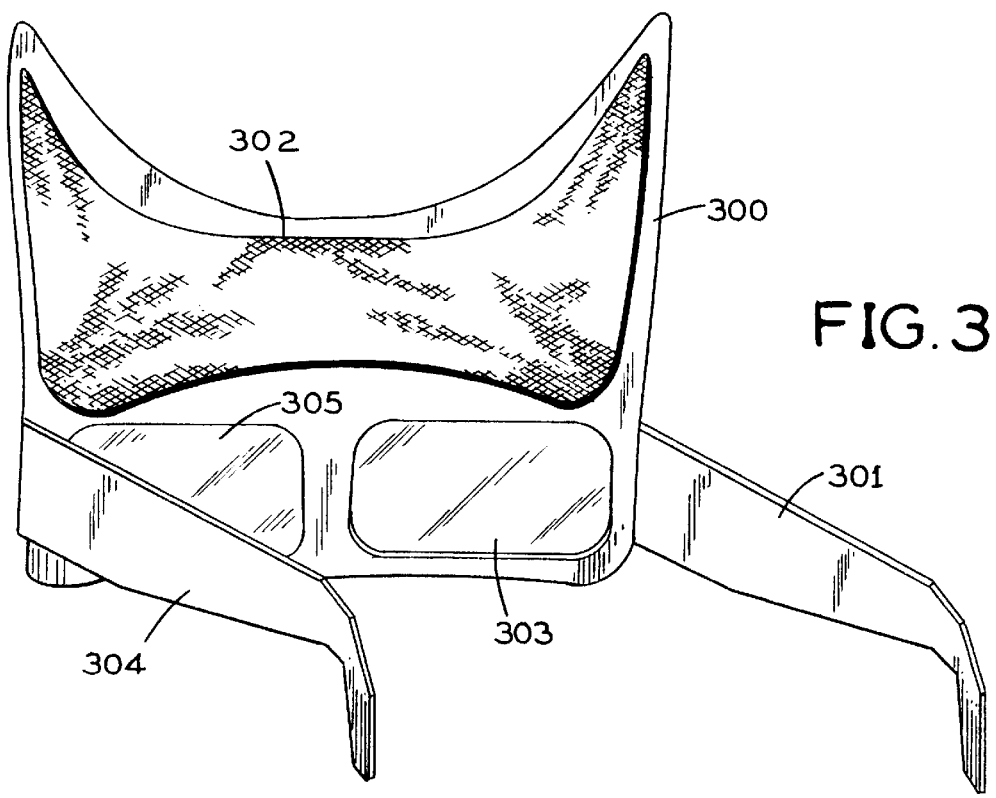
FIG. 3 shows a rear view of another embodiment of the invention.

FIG. 3 shows a rear view of another embodiment of the invention 300. A flat, planar surface made of plastic or paper is designed to generally conform to the average wearer's forehead. Ear handles 301, 304 are attached to either vertical side of the flat planar surface and extend outwardly. The ear handles 301, 304 are curved so that when folded back at their attachment point, they will fit over the wearer's ears, holding the goggles in place. At the bottom of the flat, planar surface are two eye openings 303, 305 which allow the wearer to see. These openings can be provided with clear plastic lenses to protect the wearer's eyes from the chemical hair treatment. A pad 302 similar to those depicted in FIGS. 1 or 2 is then attached to the rear of the flat, planar surface so that the invention holds the pad against the wearer's forehead.

Figure 4:
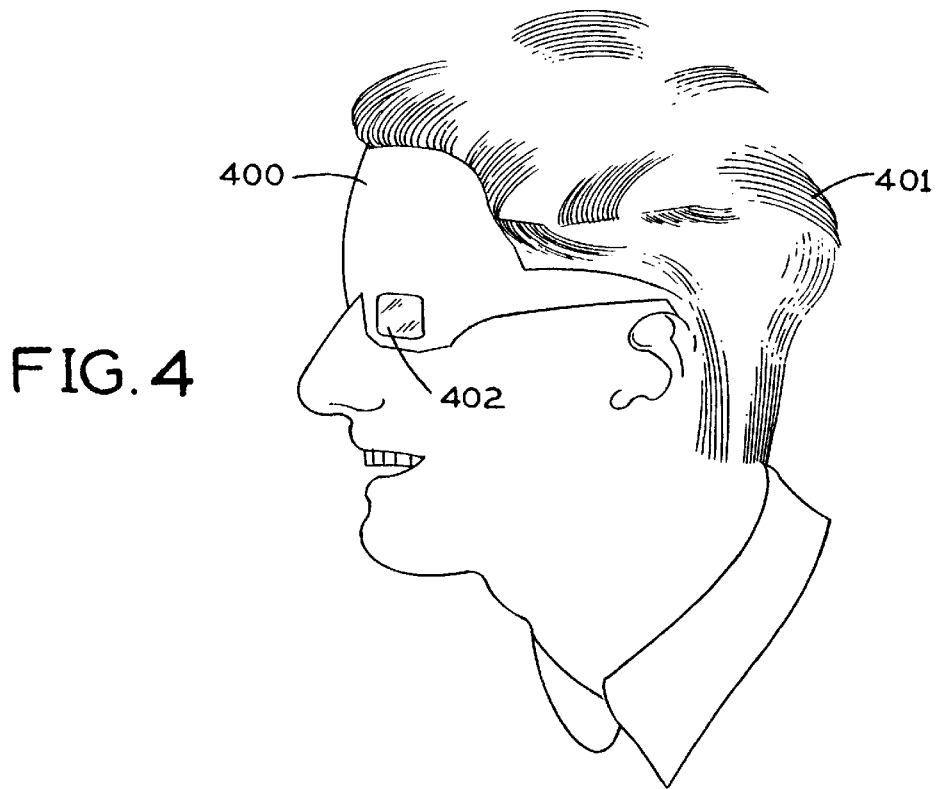
FIG. 4 shows a side view of an embodiment similar to that shown in FIG. 3 in position when used.

FIG. 4 shows a side view of an embodiment similar to that shown in FIG. 3 in position when used. This embodiment involves a more flexible support structure 400 for the pad, such that the support structure readily conforms to the wearer's forehead and face. Referring to FIGS. 3 and 4 one eye opening 305 is shown with a lens 402 in place.

Figure 5:
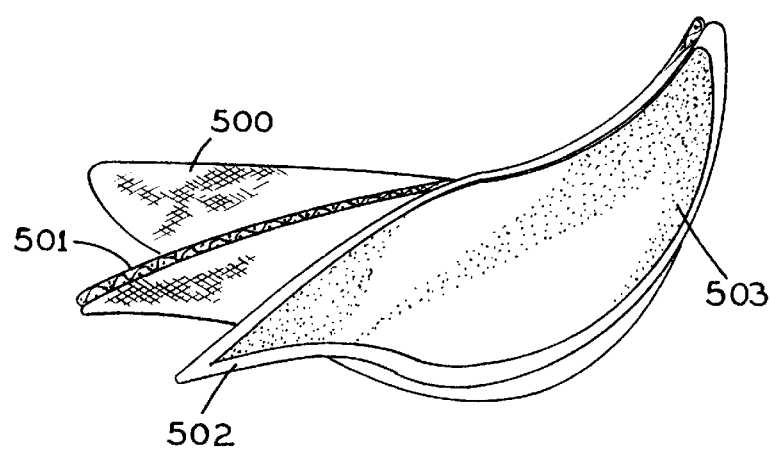
FIG. 5 shows a side view of another embodiment of the invention, with the layers peeled apart.

FIG. 5 shows a side view of another embodiment of the invention, with the layers peeled apart. The pad 500 consists of several layers attached to their adjacent layer. A highly absorbent chemical retainer layer 501, composed of cotton, paper, or other polymer based material is attached to an impermeable layer 502. The impermeable layer 502 is attached to an adhesive layer 503. The adhesive layer 503 provides a means for attaching the pad 500 to the wearer's head. Further, the absorbent layer may be constructed with air gaps which serve as capillaries so as to increase the absorbency and total retention of the pad.

Figure 6:
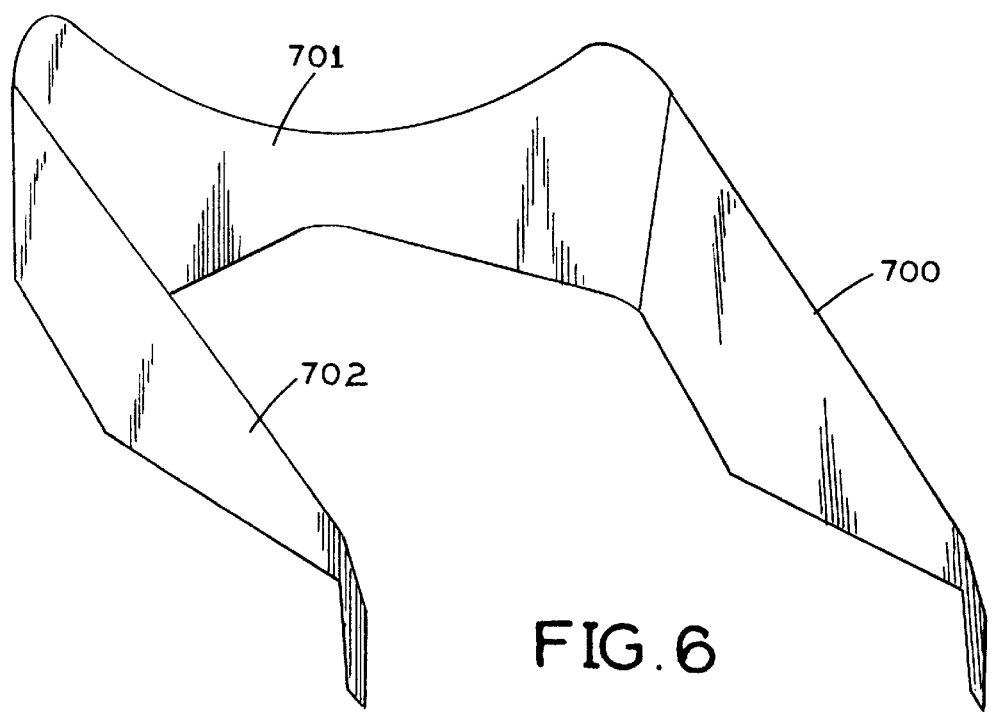
FIG. 6 shows a rear view of another embodiment of the invention.

FIG. 6 shows a rear view of another embodiment of the invention 701. Here the protective apparatus consists of a flat, planar absorbent material such as blotting paper which rests against the wearer's forehead. The absorbent material is attached to an impermeable layer. The apparatus is held in place by ear handles 700, 702 which extend outwardly in opposite directions from the sides of the apparatus and are designed to be folded back at right angles and rest against the wearer's ears. The absorbent material is held against the forehead and the user wears the apparatus as one would a pair of goggles.

Figure 7:
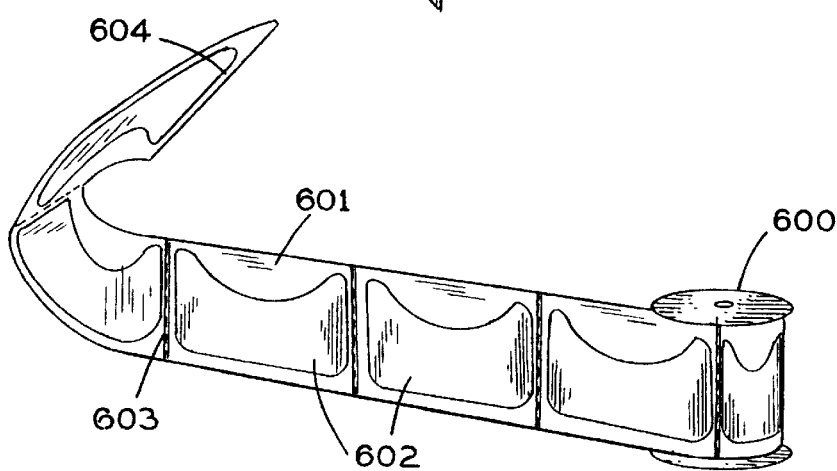
FIG. 7 shows a side view of another embodiment of the invention.

FIG. 7 shows a side view of another embodiment of the invention. This embodiment consists of any variety of the individual pads previously described. These pads are attached in series to form a single, continuous strip of pads. Each individual pad is separable from the others by a prepunched mark or line 603, enabling the user to tear off individual pads 602 as needed. These pads 602 may then be removed from the support 601 which holds the series together. This embodiment facilitates convenient storage and retrieval of the pads in the form of a roll 600.

While the invention has been described, disclosed, illustrated and shown in various terms and certain embodiments, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A protective covering for the scalp, facial skin, eyes, mouth and nostrils of a person comprising:

an absorbent, flat pad having a planar surface with a top edge and two side edges;

said top edge profiled to follow the average hairline;

said planar surface extending downwardly and outwardly from the top edge;

further comprising:
   a lining having an exterior surface and an interior surface;
   said lining being fixedly attached to and partially surrounding the pad;
   said pad being vertically longer than the lining, allowing the top edge of the pad to extend beyond the lining.

2. The protective covering of claim 1, wherein the pad includes a means of holding said pad on the forehead of a person, directly under the hairline.

3. The protective covering of claim 2, wherein the pad is constructed with air gaps which act as capillaries.

4. The protective covering of claim 1, further comprising:
   an adhesive layer fixedly attached to the exterior surface of the lining.

5. The protective covering of claim 4, wherein the pad is constructed with air gaps which act as capillaries.

6. The protective covering of claim 1, wherein the pad is constructed with air gaps which act as capillaries.

7. The protective covering of claim 1, wherein said pad comprises:
   an absorbent layer having two sides;
   an impermeable layer having two sides, one side of the impermeable layer being fixedly attached to an adjacent side of the absorbent layer.

8. The protective covering of claim 7 further comprising:
   an adhesive layer fixedly attached to an adjacent side of the impermeable layer.

9. The protective covering of claim 7, wherein the absorbent layer is constructed with air gaps which act as capillaries.

10. The protective covering of claim 8, wherein the absorbent layer is constructed with air gaps which act as capillaries.

* * * * *